United States Patent
Erman et al.

(10) Patent No.: US 7,247,743 B1
(45) Date of Patent: Jul. 24, 2007

(54) PROCESS FOR MAKING MONOMENTHYL ESTERS

(75) Inventors: Mark B. Erman, Atlantic Beach, FL (US); Joe W. Snow, Kingsland, GA (US); Mikhail Y. Lebedev, Jacksonville, FL (US)

(73) Assignee: Millennium Specialty Chemicals, Inc., Houston, TX (US)

( * ) Notice: Subject to any disclaimer, the term of this patent is extended or adjusted under 35 U.S.C. 154(b) by 0 days.

(21) Appl. No.: 11/363,446

(22) Filed: Feb. 27, 2006

(51) Int. Cl.
*C07C 69/00* (2006.01)

(52) U.S. Cl. .................................. 560/129; 560/188

(58) Field of Classification Search ............. 560/129, 560/188
See application file for complete search history.

(56) References Cited

U.S. PATENT DOCUMENTS

| 3,111,127 A | 11/1963 | Jarboe ........................ 131/17 |
| 5,725,865 A | 3/1998 | Mane et al. ................. 424/401 |
| 6,884,906 B2 | 4/2005 | Dewis et al. ............... 560/188 |

OTHER PUBLICATIONS

Takeshi Shimizu, Ryoichi Kobayashi, Hiromichi Ohmori, Tadashi Nakata Synthesis of Dicarboxylic Monoesters with Cyclic Anhydrides under High Pressure. SYNLETT, pp. 650-652, Jun. 1995.*
Dr. Junzo Otera Esterification, 2003, pp. 91-123. Wiley-VCH Verlag GmbH & Co. KGaA.*
Takeshi Shimizu, Ryoichi Kobayashi, Hiromichi Ohmori, Tadashi Nakata Synthesis of Dicarboxylic Monoesters with Cyclic Anhydrides under High Pressure. SYNLETT, pp. 650-652, Jun. 1995.*
R. Smith et al., *Food Tech. 55* (2001) 53.
H. Rule et al., *J. Chem. Soc.* (1928) 1347.
T. Hilditch, *J. Chem. Soc.* (1909) 1570.
H. Jabloner et al., *J. Polym. Sci. A. 18* (1980) 2933.
T. Shimizu et al., *Synlett* (1995) 650.

* cited by examiner

*Primary Examiner*—Johann Richter
*Assistant Examiner*—Sudhakar Katakam
(74) *Attorney, Agent, or Firm*—Jonathan L. Schuchardt

(57) ABSTRACT

A process for making monomenthyl esters of dicarboxylic acids is disclosed. Menthol reacts with a saturated, cyclic anhydride in the presence of a base catalyst under conditions effective to produce a mixture of mono- and bis-menthyl esters in which the molar ratio of mono- to bis-menthyl esters is enhanced compared with the ratio of esters produced in a similar uncatalyzed process.

8 Claims, No Drawings

PROCESS FOR MAKING MONOMENTHYL ESTERS

FIELD OF THE INVENTION

The invention relates to monomenthyl esters of dicarboxylic acids, which are valuable as physiological coolants.

BACKGROUND OF THE INVENTION

Monomenthyl esters of dicarboxylic acids such as monomenthyl succinate (MMS), monomenthyl glutarate (MMG), and monomenthyl adipate (MMA) are physiological cooling agents used in flavors, oral care and cosmetics. When prepared using l-menthol as a starting material, these half acid esters have the structures indicated below:

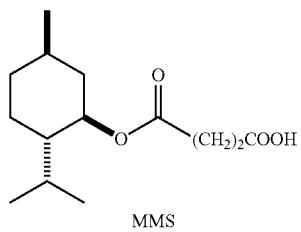

MMS

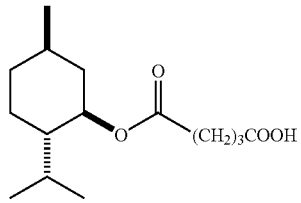

MMG

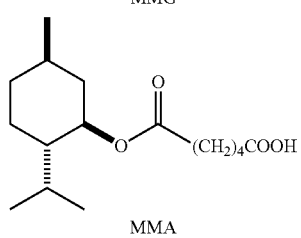

MMA

The use of these compounds as flavoring or physiological cooling agents is discussed, for example, in U.S. Pat. Nos. 5,725,865 (MMS) and 6,884,906 (MMA), and Smith et al., *Food Tech.* 55 (2001) 53 (MMG). Additionally, MMS and MMG have achieved FEMA GRAS (generally recognized as safe) status.

Despite the unquestionable value of the monomenthyl esters, relatively little is known about how to make them efficiently. In one approach (see Rule et al., *J. Chem. Soc.* (1928) 1347 and Hilditch et al., *J. Chem. Soc.* (1909) 1570), the corresponding dicarboxylic acid (e.g., succinic acid) is first reacted with an excess of thionyl chloride. Reaction of the chlorinated intermediate with excess menthol (100° C., 5-6 hours) provides a bis-menthyl ester. Finally, the bis-menthyl ester is partially hydrolyzed using sodium dissolved in 95% ethanol, and the desired monomenthyl ester is isolated in a tedious extractive workup.

The monomenthyl esters can also be made by reacting menthol with the corresponding saturated anhydride as follows:

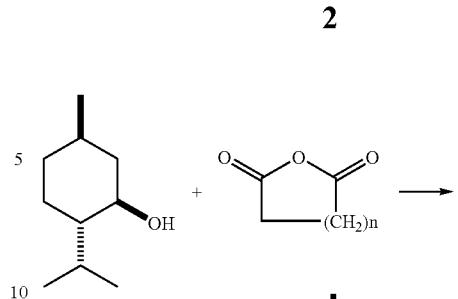

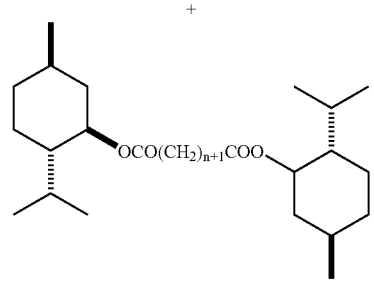

Monomenthyl esters

+

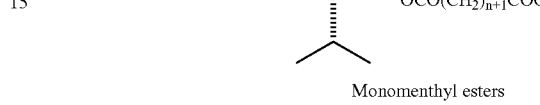

Bis-menthyl esters

Monomenthyl esters: MMS, n=1; MMG, n=2; MMA, n=3.

A few publications teach to simply heat equimolar amounts of menthol and the anhydride together in the absence of a solvent or catalyst at 110-120° C. for about one day (see, e.g., Jabloner et al., *J. Polym. Sci. A.*, 18 (1980) 2933), but none provides information about yields or selectivities to the monomenthyl ester.

U.S. Pat. No. 3,111,127 teaches a preparation of MMS from the reaction of menthol and succinic acid either uncatalyzed in refluxing chloroform, or catalyzed by p-toluenesulfonic acid in refluxing toluene. It is unclear whether the monomenthyl ester can be made efficiently by these methods, and solvents are preferably avoided for making compounds to be used in flavor or fragrance applications.

More recently, Shimizu et al. (*Synlett* (1995) 650) published a process for selectively making monomenthyl esters by using a large excess of the anhydride. Reaction of three moles of succinic anhydride with one mole of menthol in pyridine solvent in the presence of one equivalent of dimethylaminopyridine (DMAP) gave MMS in 90-97% yield. Unfortunately, the method is impractical because it requires a large excess of the anhydride, pyridine solvent, and the highly toxic DMAP.

In sum, an efficient, practical way to make monomenthyl esters of dicarboxylic acids is needed. In particular, a process that provides high selectivity to the monomenthyl ester is essential. Ideally, the process would avoid solvents or other toxic reagents and would be simple to practice.

SUMMARY OF THE INVENTION

We surprisingly found that monomenthyl esters of dicarboxylic acids, which are valuable as physiological coolants, can be made efficiently by reacting menthol with a saturated, cyclic anhydride in the presence of certain base catalysts. While the reaction provides the expected mixture of mono- and bis-menthyl esters, the process is performed under conditions effective to enhance the molar ratio of mono- to bis-menthyl esters compared with a similar uncatalyzed process.

DETAILED DESCRIPTION OF THE INVENTION

The process of the invention reacts menthol with a saturated, cyclic anhydride. Menthol suitable for use can have any desired stereochemistry. With three chiral centers, menthol has eight possible stereoisomers. A menthol sample might have several different stereoisomers present. Examples include l-menthol, d-menthol, dl-menthol (i.e., a racemic mixture of l-menthol and d-menthol), isomers of neomenthol, isomenthol, and neoisomenthol, and mixtures thereof. l-Menthol, d-menthol, dl-menthol, and other isomers are all commercially available. Because it provides monomenthyl esters having excellent physiological cooling properties, l-menthol (1) is particularly preferred.

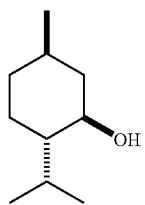

1

Suitable anhydrides are saturated, cyclic anhydrides. Preferably, the anhydride ring incorporates from two to four methylene or substituted methylene groups. Examples include succinic anhydride, glutaric anhydride, adipic anhydride, methylsuccinic anhydride, 2-phenylglutaric anhydride, 3-methylglutaric anhydride, 3-methyladipic anhydride, and the like, and mixtures thereof. Succinic anhydride, glutaric anhydride, and adipic anhydride are particularly preferred.

The relative amounts of menthol and the saturated, cyclic anhydride can vary over a fairly broad range. Preferably, however, they are used in an approximately equimolar ratio. While earlier references (see Background) recommend using at least three moles of anhydride per mole of menthol to boost the proportion of monomenthyl ester, the process of the invention provides excellent selectivity to the monomenthyl ester at much lower anhydride to menthol ratios. This is valuable because the anhydride is relatively expensive, and excess anhydride is not easily recovered or reused. Preferably, the anhydride:menthol ratio is less than about 2:1, and more preferably the anhydride:menthol ratio is within the range of 1.2:1 to 0.8:1. Most preferably, the ratio is within the range of 1.1:1 to 0.9:1.

The process is performed in the presence of a particular base catalyst. The catalyst is an alkali or alkaline earth metal salt, oxide, or hydroxide, or a mixture thereof. Preferred catalysts are alkali metal acetates, bicarbonates, carbonates, oxides, hydroxides, succinates, glutarates, and adipates. Thus, suitable catalysts include, for example, sodium carbonate, sodium bicarbonate, potassium carbonate, potassium bicarbonate, sodium hydroxide, potassium hydroxide, lithium hydroxide, sodium acetate, potassium acetate, magnesium carbonate, sodium succinate, potassium succinate, sodium glutarate, potassium glutarate, and the like. Particularly preferred catalysts, because they are inexpensive, readily available, and effective, are sodium carbonate, potassium carbonate, sodium acetate, and potassium acetate. As those skilled in the art will appreciate, the catalysts listed above may react with other components of the reaction mixture to generate new catalytic entities in-situ. For example, when sodium carbonate is added to a mixture of menthol and glutaric anhydride to produce monomenthyl glutarate (MMG), some of the MMG may lose a proton under the reaction conditions to give the monosodium salt of MMG, another base catalyst.

The amount of base catalyst needed depends on many factors, including the nature of the base, the particular anhydride used, the reaction temperature, the desired reaction time, whether or not a solvent is present, the identity of any such solvent, and other factors. Generally, however, only a catalytic amount of the base is necessary. Preferably, the catalyst is used in an amount within the range of about 0.001 to about 10 wt. % based on the amount of menthol used. A more preferred range is from about 0.01 to about 2 wt. %.

The process can be performed at any convenient temperature. Preferably, the process is performed at a temperature within the range of about 0° C. to about 200° C. A more preferred range is from about 20° C. to about 150° C.; most preferred is the range from about 50° C. to about 130° C.

Because the monomenthyl ester products will often be used in beverages, confectionary, or food applications, the process of the invention is preferably performed in the absence of a solvent. The ability to avoid a solvent is an advantage of the invention. However, a solvent may be used if desired. Suitable solvents are ones that can solubilize menthol, the cyclic anhydride, and the monomenthyl ester product. Examples include alcohols, glycols, ketones, esters, and the like, and mixtures thereof.

The use of a catalytic amount of base in the process of the invention reduces reaction time compared with uncatalyzed reactions of menthol and saturated, cyclic anhydrides. Generally, the reaction time can be cut in half or a third of the amount of time needed for the uncatalyzed reaction. As Table 1 below shows, typical reaction times might range from about one or two hours to about one day. The reaction progress can be monitored by any suitable technique, e.g., gas chromatography, to maximize the yield of monomenthyl ester.

The process selectively provides monomenthyl esters of dicarboxylic acids. Particularly preferred monomenthyl esters derive from the reaction of l-menthol and succinic, glutaric, or adipic anhydride. These monomenthyl esters have the general structure:

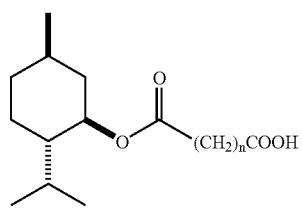

in which n has a value from 2 to 4.

The process of the invention provides a way to make high ratios of monomenthyl to bis-menthyl esters. Preferably, the molar ratio of mono- to bis-menthyl esters is at least 100% greater than the molar ratio obtained from a similar uncatalyzed process. Moreover, the molar ratio of mono- to bis-menthyl esters is preferably greater than 10. As shown in Table 1, the base-catalyzed process typically at least doubles the selectivity to monomenthyl ester when compared with the uncatalyzed reaction.

The monomenthyl esters are well known as physiological coolants. They can be used alone or in combination with other cooling agents in a wide spectrum of products, including flavors, oral care and cosmetics. For exemplary end-use applications, see, e.g., U.S. Pat. Nos. 5,725,865 and 6,884,906, the teachings of which are incorporated herein by reference. See also Smith et al. in *Food Tech.* 55 (2001) at 53.

The following examples merely illustrate the invention. Those skilled in the art will recognize many variations that are within the spirit of the invention and scope of the claims.

Selective Preparation of Monomenthyl Esters: General Procedure

A mixture of l-menthol (50 g, 0.32 mol) and glutaric anhydride (36.5 g, 0.32 mol) or succinic anhydride (32.0 g, 0.32 mol) is heated in the presence of a base catalyst (for examples of the invention) or in the absence of any catalyst (comparative examples). The reaction temperature, catalysts, and amounts are shown in Table 1. The reaction mixtures are periodically sampled and analyzed by gas chromatography (GC) to measure the conversion of menthol to the monomenthyl and bis-menthyl esters of dicarboxylic acids, i.e., monomenthyl glutarate (MMG) or monomenthyl succinate (MMS). In each case, the "monoester" reaches a maximum concentration, which slowly decreases thereafter. Maximum monoester concentrations are reported in Table 1.

The results demonstrate that the selectivity of the process for making monomenthyl esters is enhanced dramatically (100-200%) simply by including a catalytic amount of a base. Additionally, the reaction time is reduced in the presence of the catalyst. While the maximum monoester concentration is mildly enhanced by using the base catalyst, we surprisingly found that the amount of monomenthyl ester relative to the amount of bis-menthyl ester (or "diester") improves substantially when the base catalyst is included.

The examples are meant only as illustrations. The following claims define the invention.

TABLE 1

Effect of Base Catalyst on Monoester: Diester Selectivity

| Example | Product: MMG or MMS[a] | Catalyst, amount in grams | Reaction temp., °C. | Reaction time, hours[b] | Max. concentration of monoester, % (GC)[b] | Concentration of diester, % (GC)[b] | Selectivity (ratio monoester/diester)[b] |
|---|---|---|---|---|---|---|---|
| 1 | MMG | Na$_2$CO$_3$, 0.9 | 70 | 30 | 73.3 | 6.33 | 11.6 |
| C2 | MMG | None | 70 | 60 | 71.1 | 12.5 | 5.70 |
| 3 | MMG | Na$_2$CO$_3$, 0.9 | 90 | 4.5 | 76.8 | 4.44 | 17.3 |
| 4 | MMG | K$_2$CO$_3$, 1.2 | 90 | 8.0 | 75.2 | 5.87 | 12.8 |
| 5 | MMG | NaOAc, 2.0 | 90 | 5.5 | 73.6 | 5.59 | 13.2 |
| C6 | MMG | None | 90 | 17 | 73.0 | 11.2 | 6.54 |
| 7 | MMG | Na$_2$CO$_3$, 0.9 | 110 | 2.8 | 75.1 | 7.25 | 10.4 |
| 8 | MMG | NaOAc, 2.0 | 110 | 2.3 | 77.7 | 6.34 | 12.3 |
| C9 | MMG | None | 110 | 6.5 | 69.8 | 14.6 | 4.78 |
| 10 | MMS | NaOAc, 2.0 | 110 | 4.8 | 88.6 | 4.16 | 21.3 |
| C11 | MMS | None | 110 | 7.8 | 84.6 | 7.19 | 11.8 |

C = comparative example.
[a]MMG = monomenthyl glutarate, MMS = monomenthyl succinate.
[b]Maximum concentration of the monoester during the reaction.

We claim:

1. A process which comprises reacting menthol with a saturated, cyclic anhydride in the presence of a base catalyst selected from the group consisting of alkali metal or alkaline earth metal salts, oxides, hydroxides, and mixtures thereof, under conditions effective to produce a mixture of mono- and bis-menthyl esters, wherein the molar ratio of cyclic anhydride to menthol is less than 2:1, and wherein the molar ratio of mono- to bis-menthyl esters is enhanced compared with a similar uncatalyzed process.

2. The process of claim 1 wherein the anhydride is selected from the group consisting of succinic anhydride, glutaric anhydride, and adipic anhydride.

3. The process of claim 1 wherein the catalyst is selected from the group consisting of alkali metal acetates, bicarbonates, carbonates, oxides, hydroxides, succinates, glutarates, and adipates.

4. The process of claim 1 performed at a temperature within the range of about 20° C. to about 150° C.

5. The process of claim 1 wherein the catalyst is used in an amount within the range of about 0.001 to about 10 wt. % based on the amount of menthol used.

6. The process of claim 1 wherein the molar ratio of mono- to bis-menthyl esters is at least 100% greater than the molar ratio obtained from the uncatalyzed process.

7. The process of claim 1 wherein the molar ratio of mono- to bis-menthyl esters is greater than 10.

8. The process of claim 1 wherein the monomenthyl ester has the structure:

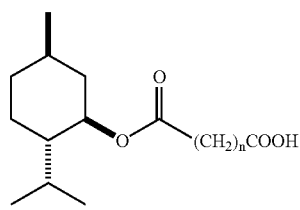

in which n has a value from 2 to 4.

* * * * *